(12) United States Patent
Kuo et al.

(10) Patent No.: US 12,311,229 B2
(45) Date of Patent: May 27, 2025

(54) METHOD, DEVICE, AND COMPUTER-READABLE STORAGE MEDIUM FOR ARRANGING EXERCISE INTENSITY

(71) Applicant: GoMore Inc., New Taipei (TW)

(72) Inventors: Hsin-Fu Kuo, New Taipei (TW); Hsin-Ju Yu, New Taipei (TW)

(73) Assignee: GoMore Inc., New Taipei (TW)

( * ) Notice: Subject to any disclaimer, the term of this patent is extended or adjusted under 35 U.S.C. 154(b) by 57 days.

(21) Appl. No.: 18/090,498

(22) Filed: Dec. 29, 2022

(65) Prior Publication Data

US 2023/0211207 A1 Jul. 6, 2023

Related U.S. Application Data (60) Provisional application No. 63/294,846, filed on Dec. 30, 2021.

(51) Int. Cl.
*A63B 24/00* (2006.01)

(52) U.S. Cl.
CPC ...... *A63B 24/0075* (2013.01); *A63B 24/0062* (2013.01); *A63B 2220/62* (2013.01); *A63B 2230/067* (2013.01); *A63B 2230/425* (2013.01)

(58) Field of Classification Search
None
See application file for complete search history.

(56) References Cited

U.S. PATENT DOCUMENTS

| | | | |
|---|---|---|---|
| 2007/0219059 A1* | 9/2007 | Schwartz | A61B 5/329 482/8 |
| 2007/0232453 A1* | 10/2007 | Hanoun | A63B 21/008 482/7 |
| 2018/0043212 A1* | 2/2018 | Shirai | A63B 24/0062 |
| 2019/0336066 A1* | 11/2019 | He | A61B 5/6897 |
| 2021/0353999 A1* | 11/2021 | Liu | G16H 40/63 |

FOREIGN PATENT DOCUMENTS

| | | | |
|---|---|---|---|
| CA | 3127656 A1 * | 8/2020 | ......... A63B 22/0076 |
| CN | 104523281 A * | 4/2015 | |
| CN | 107590358 | 1/2018 | |
| CN | 107595273 | 1/2018 | |
| CN | 111589092 | 8/2020 | |
| CN | 113066556 | 7/2021 | |
| CN | 113520313 | 10/2021 | |

(Continued)

OTHER PUBLICATIONS

CN 107590358 A. Specification Machine Translation "https://dialog.proquest.com/professional/cv_2183530/docview/1990333187/19052A2780B143E0F72/2?accountid=131444#/eng_1" Jul. 25, 2024 (Year: 2024).*

(Continued)

*Primary Examiner* — Nyca T Nguyen
(74) *Attorney, Agent, or Firm* — JCIPRNET (57) ABSTRACT

Embodiments of the disclosure provide a method, a device, and a computer-readable storage medium for arranging exercise intensity. The method includes: obtaining a user's personal information and an exercise session, where the exercise session corresponds to an exercise fatigue; and providing a recommended exercise intensity for the exercise session based on at least the personal information and the exercise fatigue.

4 Claims, 6 Drawing Sheets

---

Obtain a user's personal information and an exercise session — S210

Provide the recommended exercise intensity of the exercise session based on at least the personal information and the exercise fatigue — S220

(56) References Cited

FOREIGN PATENT DOCUMENTS

| EP | 3403572 | 11/2018 | | |
|----|---------|---------|---|---|
| JP | 2018033565 | 3/2018 | | |
| KR | 20200094449 | 8/2020 | | |
| TW | 202127362 | 7/2021 | | |
| WO | WO-2012071551 A1 * | 5/2012 | ............. | A41D 1/002 |

OTHER PUBLICATIONS

CN 107590358 A. Claim Machine Translation "https://dialog.proquest.com/professional/cv_2183530/docview/1990333187/19052A2780B143E0F72/2?accountid=131444#/eng_1" Jul. 25, 2024 (Year: 2024).*

"Office Action of Taiwan Counterpart Application", issued on Jul. 10, 2023, p. 1-p. 10.

"Notice of allowance of China Counterpart Application", issued on Jan. 6, 2025, p. 1-p. 4.

"Office Action of China Counterpart Application", issued on Jul. 23, 2024, p. 1-p. 12.

* cited by examiner

METHOD, DEVICE, AND COMPUTER-READABLE STORAGE MEDIUM FOR ARRANGING EXERCISE INTENSITY

CROSS-REFERENCE TO RELATED APPLICATION

This application claims the priority benefit of U.S. provisional application Ser. No. 63/294,846, filed on Dec. 30, 2021. The entirety of the above-mentioned patent application is hereby incorporated by reference herein and made a part of this specification.

TECHNICAL FIELD

The disclosure relates to a technique for arranging exercise content, and more particularly, to a method, a device, and a computer-readable storage medium for arranging exercise intensity.

DESCRIPTION OF RELATED ART

In modern life, it is quite common to exercise based on various exercise sessions provided by exercise-related applications. For example, the user may select a running session corresponding to a certain exercise intensity and/or exercise goal on a certain exercise application and do exercises according to the content of the running session.

However, most of the exercise sessions do not make individual adjustments for each user with different abilities. Thus, the content of the session may not be able to enable users with different abilities to achieve the required exercise intensity and/or exercise goals. As a result, all users with different abilities will take sessions with the same exercise intensity, and users with stronger abilities may find the session too easy, while users with weaker abilities may find the session too difficult, and both of them will not achieve the goals set by the session.

SUMMARY

In view of this, the disclosure provides a method, a device, and a computer-readable storage medium for arranging exercise intensity, which is capable of handling the above technical problems.

Embodiments of the disclosure provide a method for arranging exercise intensity that is adapted for a device for arranging exercise intensity, including: obtaining a user's personal information and an exercise session, where the exercise session corresponds to an exercise fatigue; and providing a recommended exercise intensity for the exercise session based on at least the personal information and the exercise fatigue.

The embodiments of the disclosure provide a device for arranging exercise intensity, which includes a storage circuit and a processor. The storage circuit stores a code. The processor is coupled to the storage circuit and accesses the code for executions of: obtaining a user's personal information and an exercise session, where the exercise session corresponds to an exercise fatigue; and providing a recommended exercise intensity for the exercise session based on at least the personal information and the exercise fatigue.

The embodiments of the disclosure provide a computer-readable storage medium recording an executable computer program, the executable computer program is loaded by a device for arranging exercise intensity for executions of: obtaining a user's personal information and an exercise session, where the exercise session corresponds to an exercise fatigue; and providing a recommended exercise intensity for the exercise session based on at least the personal information and the exercise fatigue.

DESCRIPTION OF THE EMBODIMENTS

Figure 1:
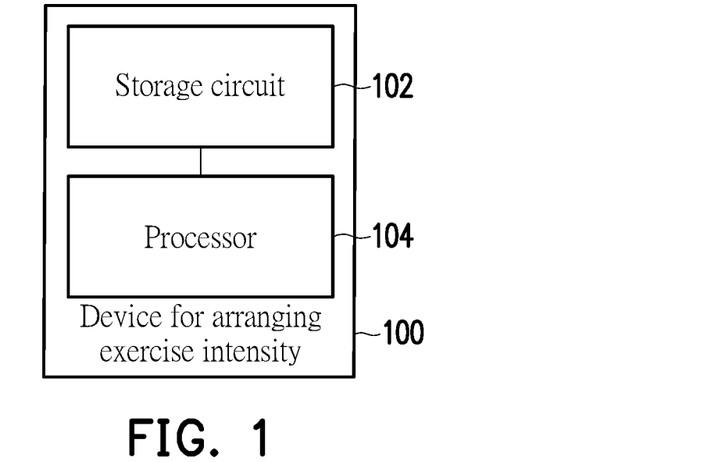
FIG. 1 is a schematic view of a device for arranging exercise intensity according to an embodiment of the disclosure.

Please refer to FIG. 1, which is a schematic view of a device for arranging exercise intensity according to an embodiment of the disclosure. In different embodiments, a device for arranging exercise intensity 100 is implemented as various smart devices and/or computer devices. The smart devices include smart mobile devices or smart wearable devices, but are not limited thereto.

In FIG. 1, the device for arranging exercise intensity 100 includes a storage circuit 102 and a processor 104. The storage circuit 102 is, for example, any type of fixed or removable random access memory (RAM), read-only memory (ROM), flash memory (Flash memory), a hard disk or other similar devices or a combination of these devices, and may be configured to record multiple codes or modules.

The processor 104 is coupled to the storage circuit 102 and may be a general purpose processor, a special purpose processor, a conventional processor, a digital signal processor, multiple microprocessors, one or more microprocessors combined with digital signal processor cores, a controller, a microcontroller, an application specific integrated circuit (ASIC), a field programmable gate array (FPGA) circuit, any other kind of integrated circuit, a state machine, an advanced risc machine-based processor, and the like.

In the embodiment of the disclosure, the processor 104 may access the module and the code recorded in the storage circuit 102 to implement the method for arranging exercise intensity proposed by the disclosure, the details of which are as follows.

Figure 2:
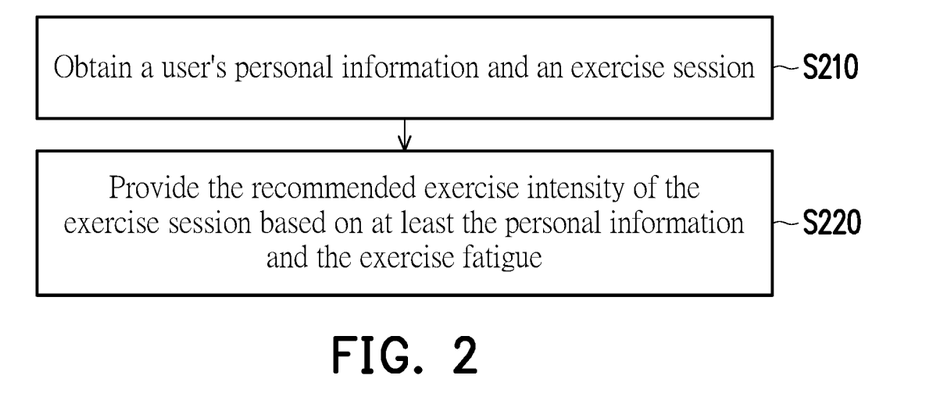
FIG. 2 is flowchart of a method for arranging exercise intensity according to an embodiment of the disclosure.

Please refer to FIG. 2, which is flowchart of a method for arranging exercise intensity according to an embodiment of the disclosure. The method of this embodiment is executed by the device for arranging exercise intensity 100 in FIG. 1. The details in FIG. 2 will be described below with the components shown in FIG. 1.

First, in step S210, the processor 104 obtains a user's personal information and an exercise session. In an embodiment, the exercise session is, for example, one of many default exercise sessions provided on an exercise application. In different embodiments, the default exercise session may include, for example, exercise items corresponding to various exercise goals and/or exercise intensity. For example, each of the default exercise sessions is set with a corresponding exercise fatigue (e.g., a rating of perceived exertion (RPE)), which is used to represent the exercise intensity corresponding to each of the default exercise sessions, but not limited thereto. The disclosure may also use other scales representing the exercise fatigue.

For convenience of description, the following embodiment assumes that the exercise session considered in step S210 is a running session, which is set with a specific RPE value as the corresponding exercise fatigue.

In addition, in different embodiments, the personal information of the user (hereinafter referred to as user A) considered in step S210 may include a maximum heart rate (hereinafter referred to as hr_max), a resting heart rate (hereinafter referred to as hr_rest), and/or a maximum oxygen consumption speed (hereinafter referred to as vVO2max) of the user A, but not limited thereto. The personal information such as hr_max, hr_rest, and vVO2max is input by the user, synchronized with cloud data, or calculated through an algorithm based on user A's daily life records or exercise records (e.g., running exercise records).

Next, in step S220, the processor 104 provides the recommended exercise intensity of the exercise session based on at least the personal information and the exercise fatigue.

In order to make the concept of the disclosure more understandable, several embodiments are supplemented below for further explanation.

Figure 3:
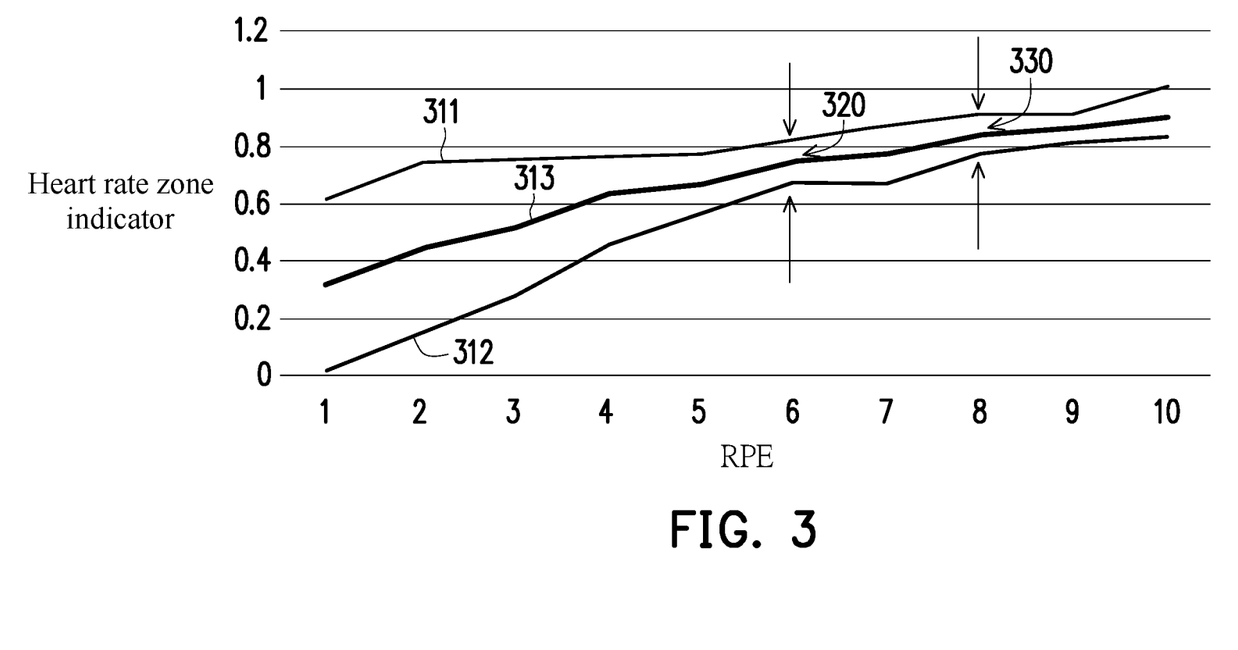
FIG. 3 is a schematic view of application scenarios according to the first embodiment of the disclosure.

Please refer to FIG. 3, which is a schematic view of application scenarios according to the first embodiment of the disclosure. In FIG. 3, the lateral axis is, for example, the RPE value; the vertical axis is, for example, the value of the heart rate zone indicator; the curve 313 is, for example, the heart rate zone indicator; the curve 311 is, for example, the upper limit of the heart rate zone indicator; and the curve 312 is, for example, the lower limit of the heart rate zone indicator.

In the first embodiment, the processor 104 may, for example, obtain the heart rate zone indicator corresponding to the exercise fatigue, and further obtain a first heart rate zone indicator (hereinafter referred to as hrz1). For example, assuming that the considered RPE value (i.e., the exercise fatigue) is 6, it is seen from FIG. 3 that the corresponding heart rate zone indicator 320 is 0.73. In this case, 0.73 is regarded as the first heart rate zone indicator. Assuming that the considered RPE value is 8, the corresponding heart rate zone indicator 330 is 0.83. In this case, 0.83 is regarded as the first heart rate zone indicator. The first heart rate zone indicators corresponding to other RPE values are deduced based on the above teachings, and details are not described herein.

After that, the processor 104 may, for example, determine a first heart rate hr1 based on a first relation formula of the first heart rate zone indicator, the maximum heart rate, the resting heart rate, and the first heart rate. The first relation formula is: hrz1=(hr1-hr_rest)/(hr_max-hr_rest) (formula (1)). Since the session has a default RPE, a first heart rate zone indicator hrz1 is obtained based on the RPE, so that the first heart rate zone indicator hrz1, the maximum heart rate hr_max, and the resting heart rate hr_rest are as known. Thus, the processor 104 may obtain the first heart rate hr1 after conversion based on the formula (1), but not limited thereto. After obtaining the first heart rate hr1 of a recommended heart rate, the processor 104 may determine the recommended exercise intensity of the exercise session accordingly.

In the second embodiment, the heart rate zone indicator corresponding to the exercise fatigue obtained by the processor 104 is between a second heart rate zone indicator (hereinafter referred to as hrz2) and a third heart rate zone indicator (hereinafter referred to as hrz3). For example, assuming that the considered RPE value (i.e., the exercise fatigue) is 6, it is seen from FIG. 3 that the corresponding heart rate zone indicator 320 is between 0.82 and 0.65. In this case, 0.82 and 0.65 are regarded as the second heart rate zone indicator and the third heart rate zone indicator respectively. Assuming that the considered RPE value is 8, the corresponding heart rate zone indicator 330 is between 0.9 and 0.76. In this case, 0.9 and 0.76 are regarded as the second and the third heart rate zone indicators respectively. The second and the third heart rate zone indicators corresponding to other RPE values are deduced based on the above teachings, and details are not described herein.

After that, the processor 104 may, for example, determine a second boundary heart rate hr2 based on a second relation formula of the second heart rate zone indicator, the maximum heart rate, the resting heart rate, and a second boundary heart rate. The second relation formula is: hrz2=(hr2-hr_rest)/(hr_max-hr_rest) (formula (2)). Since the session has a default RPE, a second heart rate zone indicator hrz2 is obtained based on the RPE, so that the second heart rate zone indicator hrz2, the maximum heart rate hr_max, and the resting heart rate hr_rest are as known. Thus, the processor 104 may obtain the second boundary heart rate hr2 after conversion based on the formula (2), but not limited thereto.

In addition, the processor 104 may, for example, determine a third boundary heart rate hr3 based on a third relation formula of the third heart rate zone indicator, the maximum heart rate, the resting heart rate, and the third boundary heart rate. The third relation formula is: hrz3=(hr3-hr_rest)/(hr_max-hr_rest) (formula (3)). Since the session has a default RPE, a third heart rate zone indicator hrz3 is obtained based on the RPE, so that the third heart rate zone indicator hrz3, the maximum heart rate hr_max, and the resting heart rate hr_rest are as known. Thus, the processor 104 may obtain the third boundary heart rate hr3 after conversion based on the formula (3), but not limited thereto.

After obtaining the second boundary heart rate hr2 and the third boundary heart rate hr3, the processor 104 may further determine the upper and lower boundaries of the recommended exercise intensity of the exercise session.

In the second embodiment, the second heart rate zone indicator hrz2 is the upper limit value obtained from the obtained data and the third heart rate zone indicator hrz3 is the lower limit value obtained from the obtained data. Thus, the second boundary heart rate hr2 is the recommended heart rate upper limit value, while the third boundary heart rate hr3 is the recommended heart rate lower limit value. In another embodiment, the processor 104 may, for example, take the greater one of the second boundary heart rate hr2 and the third boundary heart rate hr3 as the recommended heart rate upper limit value for the user A and the smaller one of the second boundary heart rate hr2 and the third boundary heart rate hr3 as the recommended heart rate lower limit value for the user A.

Based on the above embodiment, the user A may know that when exercising according to the exercise session, the heart rate should be kept at the first heart rate hr and be maintained between the second boundary heart rate hr2 and the third boundary heart rate hr3, so as to achieve the exercise fatigue corresponding to the exercise session.

Figure 4:
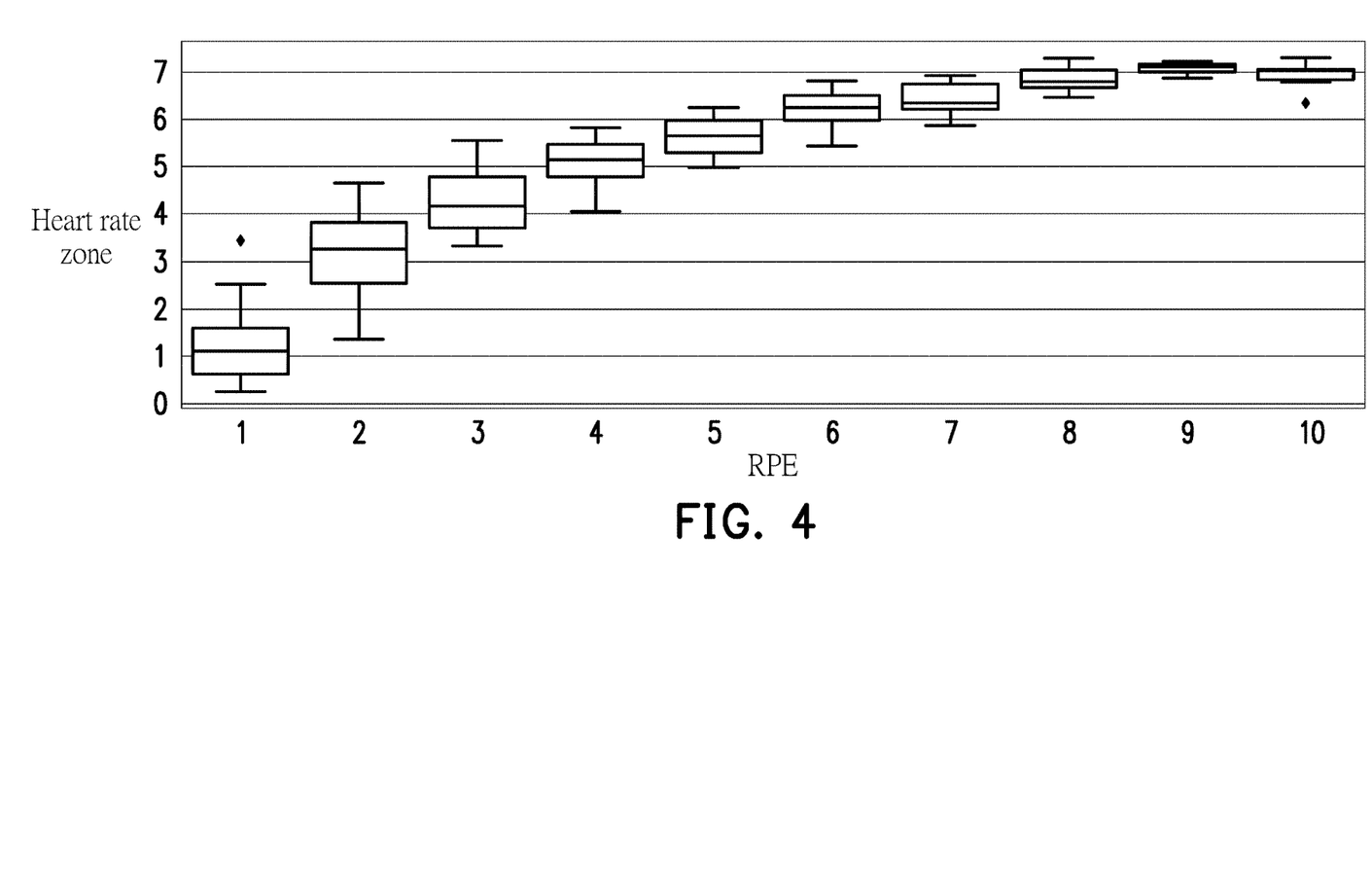
FIG. 4 is a schematic view of correspondence between running heart rate zone indicators and RPEs obtained according to the first embodiment of the disclosure.

In the first and the second embodiments, the curves 311~313 shown in FIG. 3 are obtained based on the measurement results obtained by multiple users while running. Please refer to FIG. 4. FIG. 4 is, for example, a schematic view of correspondence between running heart rate zones and RPEs obtained according to the first and the second embodiments of the disclosure. Based on the heart rate zones corresponding to each of the RPEs in FIG. 4 and the upper and lower limit values thereof, the upper and lower limit values of the heart rate zone indicator corresponding to each of the RPEs in FIG. 3 are calculated separately. Thus, curves 313, 311, and 312 are obtained respectively. The calculation method is obtained by conventional methods, which is not limited herein.

In another embodiment, different measurement results are obtained for indoor and outdoor running, and then the correspondence of indoor and outdoor RPEs and heart rate zone indicators are obtained respectively, which may correspond to indoor and outdoor running sessions respectively. For example, in response to the curves 311~313 shown in FIG. 3 corresponding to the measurement result of indoor running and the exercise session selected by the user being an indoor running session, then the first, the second, and the third heart rate zone indicators hrz1, hrz2, and hrz3 corresponding to the RPE value of the session are obtained according to the correspondence between the indoor RPE and the heart rate zone indicator. Conversely, in response to the exercise session selected by the user being an outdoor running session, hrz1, hrz2, and hrz3 corresponding to the RPE value of the session are obtained according to the correspondence between the outdoor RPE and the heart rate zone indicator. After obtaining hrz1, hrz2, and hrz3, the processor 104 may obtain the corresponding first heart rate hr1, the second boundary heart rate hr2, and the third boundary heart rate hr3 according to formulas (1), (2), and (3). For relevant details, reference may be made to the description in the first embodiment, and are not described herein.

Figure 5:
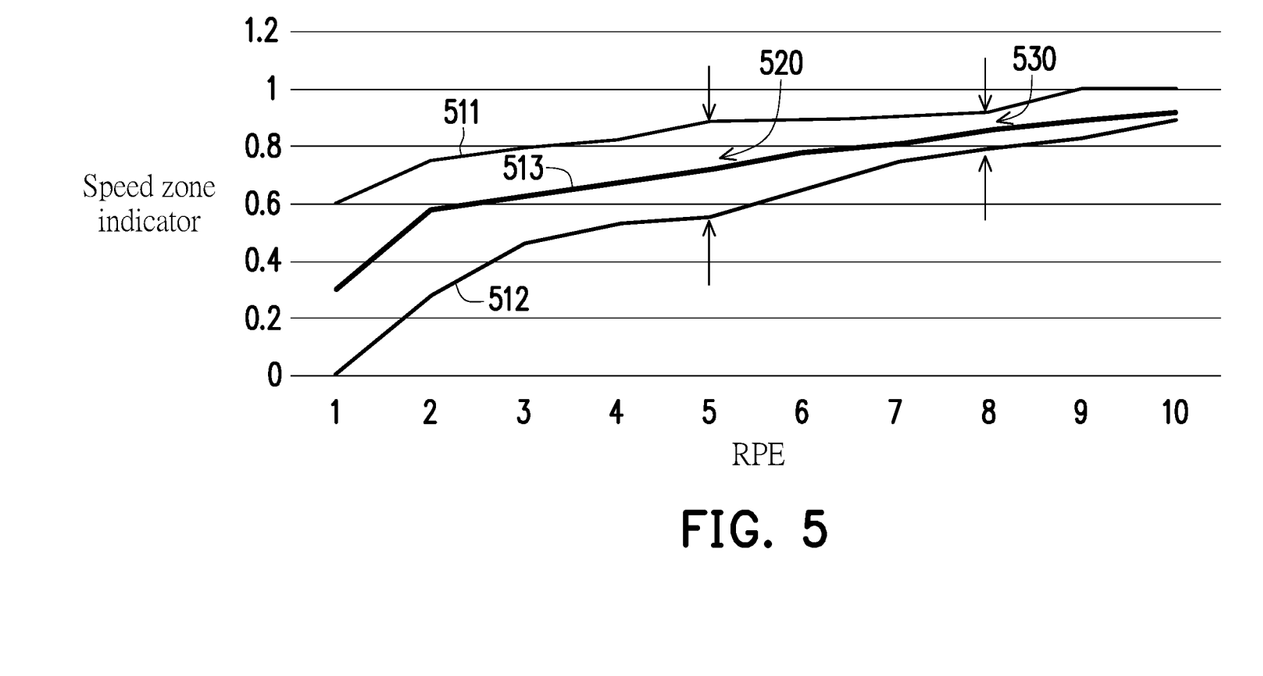
FIG. 5 is a schematic view of application scenarios according to the second embodiment of the disclosure.

Please refer to FIG. 5, which is a schematic view of application scenarios according to the third embodiment of the disclosure. In FIG. 5, the lateral axis is, for example, the RPE value; the vertical axis is, for example, the value of the speed zone indicator; 513 is, for example, the speed zone indicator; the curve 511 is, for example, the upper limit of the speed zone indicator; and the curve 512 is, for example, the lower limit of the speed zone indicator.

In the third embodiment, for example, the processor 104 may, for example, obtain the speed zone indicator corresponding to the exercise fatigue, and further obtain a first speed zone indicator (hereinafter referred to as spz1). For example, assuming that the considered RPE value (i.e., the exercise fatigue) is 5, it is seen from FIG. 5 that the corresponding speed zone indicator 520 is 0.73. In this case, 0.73 is regarded as the first speed zone indicator. Assuming that the considered RPE value (i.e., the exercise fatigue) is 8, the corresponding speed zone indicator 530 is 0.85. In this case, 0.85 is regarded as the first speed zone indicator respectively. The first speed zone indicators corresponding to other RPE values are deduced based on the above teachings, and details are not described herein.

After that, the processor 104 may determine a first speed sp1 based on a fourth relation formula of the first speed zone indicator and the maximum oxygen consumption speed vVO2max. The fourth relation formula is: spz1=sp1/vVO2max (formula (4)). Since the session has a default RPE, a first speed zone indicator spz1 is obtained based on the RPE, so that the first speed zone indicator spz1 and the maximum oxygen consumption speed vVO2max are as known. Thus, the processor 104 may obtain the first speed sp1 after conversion based on the formula (4), but not limited thereto. The first speed sp1 of the recommended speed is obtained.

In the fourth embodiment, the speed zone indicator corresponding to the exercise fatigue is obtained by the processor 104. The speed zone indicator is between a second speed zone indicator (hereinafter referred to as spz2) and a third speed zone indicator (hereinafter referred to as spz3). For example, assuming that the considered RPE value (i.e., the exercise fatigue) is 5, it is seen from FIG. 5 that the corresponding speed zone indicator 520 is between 0.9 and 0.55. In this case, 0.9 and 0.55 are regarded as the second speed zone indicator and the third speed zone indicator respectively. Assuming that the considered RPE value (i.e., the exercise fatigue) is 8, the corresponding speed zone indicator 530 is between 0.91 and 0.79. In this case, 0.91 and 0.79 are regarded as the second and the third speed zone indicators respectively. The second and the third speed zone indicators corresponding to other RPE values are deduced based on the above teachings, and details are not described herein.

After that, the processor 104 may determine a second boundary speed sp2 based on a fifth relation formula of the second speed zone indicator and the maximum oxygen consumption speed vVO2max. The fifth relation formula is: spz2=sp2/vVO2max (formula (5)). Since the session has a default RPE, a second speed zone indicator spz2 is obtained based on the RPE, so that the second speed zone indicator spz2 and the maximum oxygen consumption speed vVO2max are as known. Thus, the processor 104 may obtain the first boundary speed sp2 after conversion based on the formula (5), but not limited thereto.

In addition, the processor 104 may, for example, determine a third boundary speed sp3 based on a sixth relation formula of the third speed zone indicator, the maximum oxygen consumption speed vVO2max, and the second boundary speed. The sixth relation formula is: spz3=sp3/vVO2max (formula (6)). Since the session has a default RPE, a second speed zone indicator spz2 is obtained based on the RPE, so that the third speed zone indicator spz3 and the maximum oxygen consumption speed vVO2max are as known. Thus, the processor 104 may obtain the third boundary speed sp3 after conversion based on the formula (6), but not limited thereto.

After obtaining the second boundary speed sp2 and the third boundary speed sp3, the processor 104 may further determine the upper and lower boundaries of the recommended exercise intensity of the exercise session.

In the fourth embodiment, the second speed zone indicator spz2 is the upper limit value obtained from the obtained data and the third speed zone indicator spz3 is the lower limit value obtained from the obtained data. Thus, the second boundary speed sp2 is the recommended speed upper limit value, while the third boundary speed sp3 is the recommended speed lower limit value. In another embodiment, the processor 104 may, for example, take the greater value of the second boundary speed sp2 and the third boundary speed sp3 as the recommended speed upper limit value for the user A and the smaller one of the second boundary speed sp2 and the third boundary speed sp3 as the recommended speed lower limit value for the user A.

Based on the above embodiment, the user A may know that when exercising according to the exercise session, the speed should be kept at the first speed sp1 and be maintained between the second boundary speed sp2 and the third boundary speed sp3, so as to achieve the exercise fatigue corresponding to the exercise session. It is seen from the above that the method proposed by the embodiments of the disclosure give personalized exercise intensity recommendation to the user, including heart rate or speed recommendations, so as to help the user achieve the required exercise fatigue, and then achieve the required exercise intensity and/or exercise goal.

Figure 6:
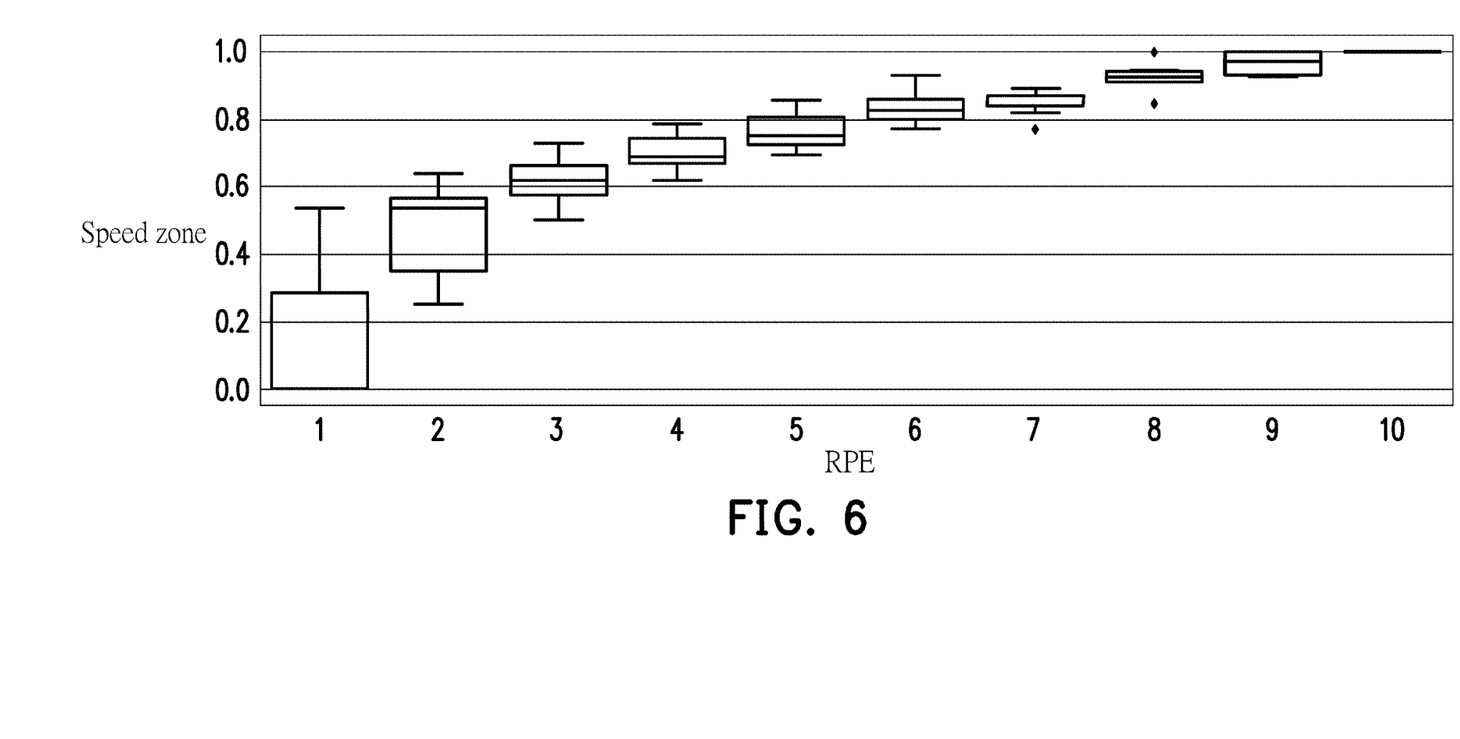
FIG. 6 is a schematic view of correspondence between running speed zones and RPEs obtained according to the second embodiment of the disclosure.

In the third and the fourth embodiments, the curves 511~513 shown in FIG. 5 are obtained based on the measurement results obtained by multiple users while running. Please refer to FIG. 6. FIG. 6 is, for example, a schematic view of correspondence between running speed zones and RPEs obtained according to the third and the fourth embodiments of the disclosure. Based on the upper and lower limit values of the speed zones corresponding to each of the RPEs in FIG. 6, the speed zones corresponding to each of the RPEs in FIG. 5 and the upper and lower limit values thereof are calculated respectively. The upper and lower limit values of the speed zone indicators corresponding to each of the RPEs in FIG. 5 are also calculated, and curves 513, 511, and 512 are further obtained respectively. The calculation method is obtained by conventional methods, which is not limited herein.

In another embodiment, different measurement results are obtained for indoor and outdoor running, and then the correspondence of indoor and outdoor RPEs and speed zone indicators are obtained respectively, which may correspond to indoor and outdoor running sessions respectively. For example, in response to the curves 511~513 shown in FIG. 5 corresponding to the measurement result of indoor running and the exercise session selected by the user being an indoor running session, then the first, the second, and the third speed zone indicators spz1, spz2, and spz3 corresponding to the RPE value of the session are obtained according to the correspondence between the indoor RPE and the speed zone indicator. Conversely, in response to the exercise session selected by the user being an outdoor running session, the first, the second, and the third speed zone indicators spz1, spz2, and spz3 corresponding to the RPE value of the session are obtained according to the correspondence between the outdoor RPE and the speed zone indicator. After spz1, spz2, and spz3, the processor 104 may obtain the corresponding first speed sp1, second boundary speed sp2, and third boundary speed sp3 according to formulas (5) and (6). For relevant details, reference may be made to the description in the first embodiment, and are not described herein.

Figure 7:
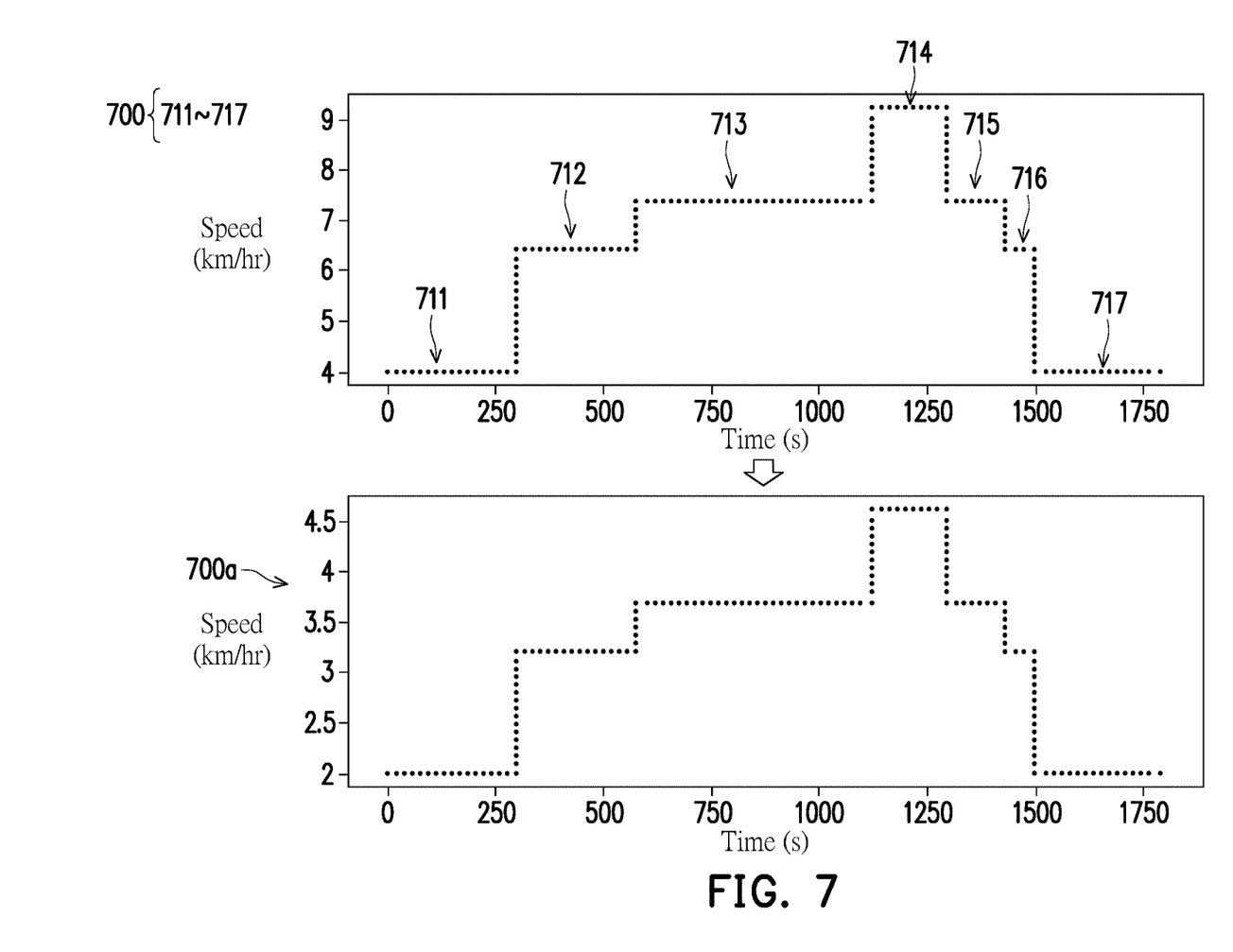
FIG. 7 is a schematic view of scaled exercise speeds according to the second embodiment of the disclosure.

Please refer to FIG. 7, which is a schematic view of scaled exercise speeds according to the second embodiment of the disclosure. In FIG. 7, an exercise session 700 is, for example, divided into multiple time intervals 711~717, and each of the time intervals 711~717 may correspond to a default specified exercise speed/intensity.

For example, the specified exercise speed corresponding to the time interval 711 is, for example, 4 km/hr; the specified exercise speed corresponding to the time interval 712 is, for example, 6.5 km/hr; and the specified exercise speed corresponding to the time interval 713 is, for example, 7.5 km/hr. The specified exercise speeds corresponding to other time intervals 714~717 are deduced based on the above teachings, and details are not described herein.

In an embodiment, the processor 104 may find out the maximum exercise speed of the exercise session 700 from the specified exercise speed corresponding to each of the time intervals 711~717 and use the maximum exercise speed as the representative speed corresponding to the default RPE of the exercise session 700. Taking FIG. 7 as an example, the maximum exercise speed of the exercise session 700 is, for example, the specified exercise speed (9 km/hr) corresponding to the time interval 714 and the default RPE is 2. Afterwards, in an embodiment, assuming that the recommended speed is the first speed sp1. In another embodiment, it is recommended that the upper limit speed is the second boundary speed sp2 and the lower limit speed is third boundary speed sp3. Thus, the processor 104 may, for example, obtain a scaling factor by dividing the maximum exercise speed by the user's personal first speed sp1 corresponding to the RPE of the session. In the scenario of FIG. 7, in response to the first speed sp1 corresponding to the REP of 2 being 4.5 km/hr and the maximum exercise speed being 9 km/hr, the processor 104 may determine that the scaling factor is 2 (i.e., 9/4.5).

Next, the processor 104 may scale the specified exercise speed corresponding to each of the time intervals 711~717 based on the scaling factor. For example, the processor 104 may scale the specified exercise speed corresponding to each of the time intervals 711~717 by dividing the specified exercise speed corresponding to each of the time intervals 711~717 by the scaling factor.

In FIG. 7, assuming that the scaling factor is 2, the specified exercise speed corresponding to each of the time intervals 711~717 after scaling is adjusted as shown in the exercise session 700a. In another embodiment, the upper and lower limits of the specified exercise speed corresponding to each of the time intervals 711~717 are also recommended at the same time for the user's reference. In an embodiment, the recommended exercise speed and the upper and lower limits thereof are displayed on a wearable device, such as a watch or a wristband, and the users may confirm the above-mentioned at any time when exercising.

It is seen from the above that the embodiments of the disclosure may convert the exercise session 700 into a personalized version corresponding to the user A (e.g., the exercise session 700a) according to the first speed, the second boundary speed, and/or the third boundary speed corresponding to the RPE of the exercise session 700 selected by the user A. In response to exercising according to the exercise speed set by the original exercise session 700, that is, a maximum exercise speed of 9 km/hr, then although the default exercise fatigue RPE of the exercise session is 2, the user may feel that the exercise intensity is too high, causing the RPE to be well above 2. In the case of adjusting the speed through the disclosure, the user A may exercise according to the exercise session 700a, that is, the maximum exercise speed is adjusted to 4.5 km/hr and other exercise speeds are adjusted accordingly, so as to achieve the exercise fatigue RPE of 2 corresponding to the exercise session. Considering the above, the method proposed by the embodiments of the disclosure gives the user A personalized exercise speed recommendations, and after user A is trained according to the session, an expected exercise fatigue is obtained.

In addition, the disclosure provides a computer-readable storage medium for executing the method for arranging exercise intensity. The computer-readable storage medium includes multiple program instructions implemented therein (e.g., program setting instructions and program deploying instructions). The program instructions are loaded into the device for arranging exercise intensity 100 and executed by the device for arranging exercise intensity 100, so as to perform the method for arranging exercise intensity and the functions of the device for arranging exercise intensity 100.

To sum up, the method of the embodiment of the disclosure is used after the user selects the exercise session. The user is provided with the corresponding recommended exercise intensity (e.g., the exercise speed and/or the heart rate) according to the exercise fatigue corresponding to the exercise session and the user's personal information (e.g., the maximum heart rate, the resting heart rate, and/or the maximum oxygen consumption speed), In this way, the method of the embodiment of the disclosure provides the user with more personalized exercise recommendations, thereby helping the user to achieve the desired exercise goal and/or exercise intensity.

Although the disclosure has been described in detail with reference to the above embodiments, they are not intended to limit the disclosure. Those skilled in the art should understand that it is possible to make changes and modifications without departing from the spirit and scope of the disclosure. Therefore, the protection scope of the disclosure shall be defined by the following claims.

What is claimed is:

1. A device for arranging exercise intensity, comprising:
   a storage circuit storing a code; and
   a processor coupled to the storage circuit and accessing the code for executions of:
   providing various exercise sessions on an exercise application to a user, wherein each exercise session corresponding to an exercise fatigue;
   obtaining a first exercise session from the various exercise session, wherein the first exercise session corresponds to a first exercise fatigue;
   obtaining a user's personal information, wherein the personal information of the user comprises a maximum oxygen consumption speed (vVO2max) of the user;
   obtaining a first speed zone indicator corresponding to the first exercise fatigue;
   determining a first speed based on the first speed zone indicator and the personal information;
   determining a recommended exercise intensity of the first exercise session based on the first speed; and
   providing the recommended exercise intensity of the first exercise session and displaying on a wearable device.

2. The device according to claim 1, wherein the device for arranging exercise intensity is the wearable device.

3. A computer-readable storage medium recording an executable computer program, the executable computer program is loaded by a device for arranging exercise intensity for executions of:
   providing various exercise sessions on an exercise application to a user, wherein each exercise session corresponding to an exercise fatigue;
   obtaining a first exercise session from the various exercise session, wherein the first exercise session corresponds to a first exercise fatigue;
   obtaining a user's personal information, wherein the personal information of the user comprises a maximum oxygen consumption speed (vVO2max) of the user;
   obtaining a first speed zone indicator corresponding to the first exercise fatigue;
   determining a first speed based on the first speed zone indicator and the personal information;
   determining a recommended exercise intensity of the first exercise session based on the first speed; and
   providing the recommended exercise intensity of the first exercise session and displaying on a wearable device.

4. The computer-readable storage medium according to claim 3, wherein the device for arranging exercise intensity is the wearable device.

* * * * *